(12) United States Patent
Chi et al.

(10) Patent No.: US 11,986,238 B2
(45) Date of Patent: May 21, 2024

(54) NON-PUNCTURING MICROWAVE ABLATION ANTENNA AND APPLICATION THEREOF

(71) Applicant: MIMA-PRO (NAN TONG) SCIENTIFIC INC, Nantong (CN)

(72) Inventors: Jiachang Chi, Nantong (CN); Bo Zhai, Nantong (CN); Peng Zhang, Nantong (CN); Ting Yang, Nantong (CN)

(73) Assignee: MIMA-PRO (NAN TONG) SCIENTIFIC INC, Nantong (CN)

( * ) Notice: Subject to any disclaimer, the term of this patent is extended or adjusted under 35 U.S.C. 154(b) by 858 days.

(21) Appl. No.: 17/044,145

(22) PCT Filed: Mar. 12, 2019

(86) PCT No.: PCT/CN2019/077763
§ 371 (c)(1),
(2) Date: Sep. 30, 2020

(87) PCT Pub. No.: WO2019/223400
PCT Pub. Date: Nov. 28, 2019

(65) Prior Publication Data
US 2021/0113267 A1    Apr. 22, 2021

(30) Foreign Application Priority Data

May 25, 2018    (CN) .......................... 201810516456.1

(51) Int. Cl.
*A61B 18/18*    (2006.01)
*A61B 17/00*    (2006.01)
(Continued)

(52) U.S. Cl.
CPC ................... *A61B 18/1815* (2013.01); *A61B 2017/00862* (2013.01); *A61B 2017/3456* (2013.01);
(Continued)

(58) Field of Classification Search
CPC .......... A61B 18/1815; A61B 2018/183; A61B 17/3496; A61B 2017/00862;
(Continued)

(56) References Cited

U.S. PATENT DOCUMENTS

| 2007/0203480 A1* | 8/2007 | Mody | ................ | A61B 18/1815 606/33 |
| 2016/0095657 A1* | 4/2016 | Brannan | ............ | A61B 18/1815 606/33 |

(Continued)

FOREIGN PATENT DOCUMENTS

| CN | 103340684 A | 10/2013 |
| CN | 203493740 U | 3/2014 |

(Continued)

*Primary Examiner* — Sean W Collins
(74) *Attorney, Agent, or Firm* — Bayramoglu Law Offices LLC

(57) ABSTRACT

A non-puncturing microwave ablation antenna, including an irradiator located at a front end of the antenna and an irradiator cover sleeved on the irradiator, where a front end of the irradiator cover is blunt. Because the front end of the irradiator cover is designed to be blunt, the special non-puncturing appearance of the irradiator cover enables the antenna to freely penetrate inside the lung tissue without puncturing blood vessels and bronchi in the lungs. In addition, blood vessels of tumor existing in the Ground-Glass Opacity (GGO) would not be damaged by the blunt head and bleed, thereby reducing a rate of surgery failure caused by that a lesion cannot be identified because of bleeding inside the lung, and in addition, avoiding a possibility that tumor cells spread through a puncturing passage or bleeding blood vessels.

16 Claims, 1 Drawing Sheet

(51) Int. Cl.
*A61B 17/34* (2006.01)
*A61B 18/00* (2006.01)

(52) U.S. Cl.
CPC .................. *A61B 17/3496* (2013.01); *A61B 2018/00011* (2013.01); *A61B 2018/00035* (2013.01); *A61B 2018/00178* (2013.01); *A61B 2018/00541* (2013.01); *A61B 2018/00577* (2013.01); *A61B 2018/183* (2013.01); *A61B 2018/1869* (2013.01)

(58) Field of Classification Search
CPC .......... A61B 2018/00035; A61B 2018/00178; A61B 2018/00541; A61B 2018/00577; A61B 2018/1869
See application file for complete search history.

(56) References Cited

U.S. PATENT DOCUMENTS

| | | | | |
|---|---|---|---|---|
| 2017/0252106 | A1* | 9/2017 | Brannan | A61B 18/1815 |
| 2018/0214012 | A1* | 8/2018 | Krimsky | A61B 1/015 |
| 2019/0380777 | A1* | 12/2019 | Huang | A61B 18/1815 |
| 2020/0069368 | A1* | 3/2020 | Huang | A61B 18/1815 |

FOREIGN PATENT DOCUMENTS

| | | |
|---|---|---|
| CN | 104042342 A | 9/2014 |
| CN | 204600679 U | 9/2015 |
| CN | 107260301 A | 10/2017 |
| CN | 108670405 A | 10/2018 |

* cited by examiner

NON-PUNCTURING MICROWAVE ABLATION ANTENNA AND APPLICATION THEREOF

CROSS REFERENCE TO THE RELATED APPLICATIONS

This application is the national stage entry of International Application No. PCT/CN2019/077763, filed on Mar. 12, 2019, which is based upon and claims priority to Chinese Patent Application No. 201810516456.1, filed on May 25, 2018, the entire contents of which are incorporated herein by reference.

TECHNICAL FIELD

The present invention relates to a microwave ablation antenna and an application thereof, and belongs to the field of microwave ablation technologies.

BACKGROUND

With the advancement of modern technologies and oncology, breakthroughs have been made in the microwave tumor ablation technology in China and abroad in the past decade. As such a local treatment means for tumors that is truly minimally invasive is widely applied, thermal ablation has now become a first-line, preferred treatment manner in clinical treatment guidelines, and liver cancer, lung cancer, and thyroid adenoma are hotspot fields of microwave ablation. Microwave tumor ablation is using microwave energy to act on tissue to produce a thermal effect, where in a few minutes to tens of minutes, a center temperature of a thermal field of microwave tumor ablation can reach 100° C. or above, and tumor tissue is coagulated and inactivated at an instant high temperature, to achieve an objective of tumor ablation treatment. Microwave tumor ablation is to insert a microwave ablation needle into a lesion of human tissue, where the microwave ablation needle continuously emits microwave energy from a front end thereof to perform surgery, and because microwave tumor ablation has high efficiency and causes a small wound, and a depth and a scope of an effect of microwave tumor ablation on tissue are controllable, microwave tumor ablation is suitable for ablation surgeries for solid tumors throughout the body.

Lung ground-glass opacity (GGO) in chest CT shows a cloud-like light shadow/round nodule with a slight increase in density, looks like ground glass, and therefore, is referred to as GGO. GGO may grow diffusely or may only gather locally, and looks like a small ground glass nodule. Generally, most GGOs that grow diffusely are benign lesions, while GGOs that grow locally are likely to be lung cancer. With the popularization and clinical application of CT, especially, the wide application in physical examination, GGO shows an explosive growth trend globally. Due to the convenience of CT examination, GGO lesions have been clearly defined as precancerous lesions or early cancers, and there have been generally accepted imaging standards for staging and guiding clinical treatment.

A gold standard of conventional GGO treatment is surgical resection. At present, thoracoscopic partial lung resection is widely used in clinical practice. Due to the particularity of GGO tissue, a positioning device (a metal object in a shape similar to a hook) is generally inserted into the lungs to reach the GGO before surgery, and then, the surgery is performed. Although thoracoscopic surgery causes a relatively small wound in appearance, a surgical method is still surgical resection. To remove a small lesion with a diameter of one centimeter, it is often necessary to remove a whole piece of wedge-shaped lung tissue around. In addition, due to the damage to the chest wall and pleural tissue, the patient may suffer from great pain, and this is not conducive to recovery of the patient. After the emergence of the microwave ablation technology, biopsy is usually performed on cells through puncturing first, and then, microwave ablation is performed. Puncturing needles are used in both biopsy and ablation. A sharp needle tip may damage blood vessels and bronchi. Once blood vessels are punctured, the blood flowing out makes it difficult for GGO to be clearly identified in imaging, which increases difficulty in surgery. Moreover, a biopsy needle may puncture through the entire tissue of GGO, resulting in a break of a natural barrier between normal tissue and tumor cells. At the same time, due to bleeding, cancer cells may also enter the blood system to reach other tissues of the body and consequently, spread. Therefore, compared with thoracoscopic surgery, such a surgical method minimizes damage to normal lung tissue and also brings less pain to the patient, but bleeding in the lungs causes a problem of difficulty in clearly identifying GGO and a risk of cancer spreading.

SUMMARY

The technical problem to be resolved by the present invention is to overcome the foregoing defects of the prior art and provide a non-puncturing microwave ablation antenna, capable of directly performing microwave ablation without puncturing tumor tissue and internal blood vessels, which is particularly suitable for treatment of GGO.

To resolve the foregoing technical problem, the present invention provides a non-puncturing microwave ablation antenna, including an irradiator located at a front end of the antenna and an irradiator cover sleeved on the irradiator, where a front end of the irradiator cover is blunt. Therefore, the antenna can be inserted into lung tissue of the lungs without puncturing blood vessels and bronchi in the lung. In addition, a lesion can be squeezed and pushed with a blunt needle tip, and the lesion further compressed by utilizing the feature that a GGO has tissue characteristics close to those of the lung tissue and is elastic, and is wrapped around the head of the ablation needle after being smaller. Therefore, the tumor can be completely killed within a smaller ablation range without puncturing through the lesion. There is no central needle passage penetrating through the center of the lesion, to prevent the central needle passage and severely degenerated tissue beside the needle passage from affecting pathological biopsy sampling.

Further, a groove is provided in a sidewall of the irradiator cover, and the groove is provided close to the irradiator.

In addition, the present invention further claims application of the non-puncturing microwave ablation antenna in microwave ablation treatment of lung GGO. In microwave ablation treatment of lung GGO by using the non-puncturing microwave ablation antenna, a lesion is squeezed to be compressed and wrapped around the head of the ablation needle, to reduce an ablation range, protect normal lung tissue, and prevent the ablation needle passage in the center of the lesion from affecting pathological biopsy sampling.

Because the front end of the irradiator cover is designed to be blunt, the special non-puncturing appearance of the irradiator cover enables the antenna to freely penetrate inside the lung tissue without puncturing blood vessels and bronchi in the lungs. Due to the particularity of the lung tissue, even though the front end of the irradiator cover is blunt, the antenna can still be easily inserted into the interior of the GGO tissue in the lungs. In addition, blood vessels of tumor existing in the GGO would not be damaged by the blunt head and bleed, thereby reducing a rate of surgery failure caused by that a lesion cannot be identified because of bleeding inside the lung, and in addition, avoiding a possibility that tumor cells spread through a puncturing passage or bleeding blood vessels, which is more adapted to the no touch principle in current tumor treatment.

The blunt front end can squeeze the GGO lesion without penetrating through the GGO, to make the lesion denser while obviously reducing a volume of the lesion, thereby reducing a range of ablation to protect the lung tissue to the greatest extent. After the ablation surgery is completed, biopsy of the GGO tissue is performed again to better avoid bleeding caused by puncturing, and increase a quantity of specimens collected by biopsy for determining a pathological tissue type and a degree of infiltration of the GGO. Because the present invention is different from the conventional mode of penetrating a lesion and then performing ablation, the present invention further prevents an ablation needle passage in the middle of the lesion from affecting pathological biopsy sampling. The passability and safety of the blunt non-puncturing head in the lung tissue are confirmed through preliminary animal experiments. Biopsy after clinical GGO microwave ablation also confirms that a positive rate, a specimen length, and a complication rate of biopsy after ablation are better than those of pathological biopsy before ablation.

In view of the above, when the microwave antenna of the present invention is used to perform treatment of GGO, to avoid bleeding in the lungs, ablation treatment can be completed without puncturing the GGO tissue, and has higher safety. In addition, a groove is provided in a sidewall of the irradiator cover. After GGO ablation is completed, tissue at the GGO appears to protrude outward and therefore, is more likely to be found, thereby improving accuracy of biopsy sampling.

BRIEF DESCRIPTION OF THE DRAWINGS

The present invention is further described below with reference to the accompanying drawings.

Figure 1:
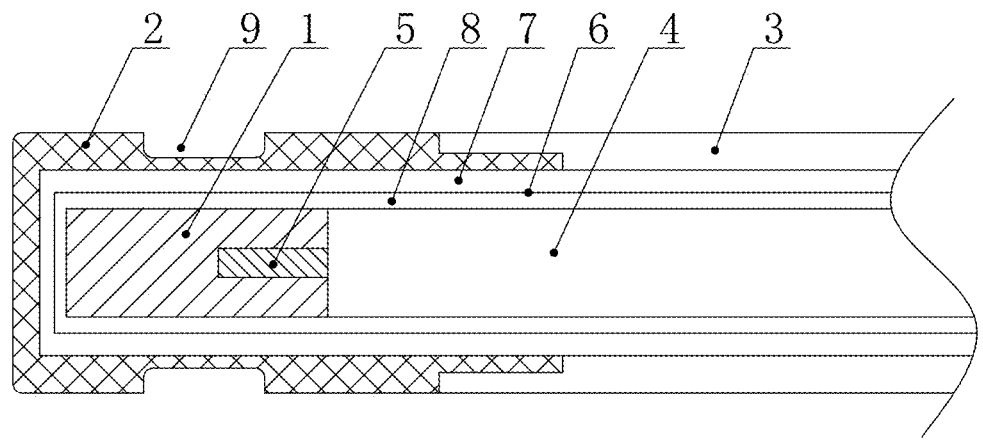
FIG. 1 is a partial cross-sectional view of a front end of a microwave ablation antenna according to Embodiment 1.

Reference signs in the drawing are described as follows: 1-irradiator, 2-irradiator cover, 3-needle bar, 4-outer conductor, 5-inner conductor, 6-medium pipe, 7-first gap, 8-second gap, 9-groove, 10-medium sleeve, 11-water plugging shaft, 12-water guide pipe.

DETAILED DESCRIPTION OF THE EMBODIMENTS

To make objectives, technical solutions, and advantages of the embodiments of the present invention clearer, the technical solutions in the embodiments of the present invention are described below clearly and completely with reference to accompanying drawings in the embodiments of the present invention.

Embodiment 1

As shown in FIG. 1, a non-puncturing microwave ablation antenna of this embodiment includes a non-puncturing irradiator of a front end of the antenna and an irradiator cover 2 sleeved on an irradiator 1. The entire irradiator cover 2 is made from an elastic material. The irradiator cover 2 in this embodiment is made from PI, and in addition, the irradiator cover 2 may alternatively be made from polyetheretherketone (PEEK) or zirconia porcelain (a non-elastic material). An advantage of using the elastic material is that: after the antenna is inserted into the lungs, blood vessels or bronchi are not damaged, and bleeding in the lungs is not caused. Therefore, a preferred solution is that design requirements of the present invention can be satisfied provided that at least the front end of the irradiator cover is made from an elastic material. The thickness of the irradiator cover is 0.35 mm, and the irradiator cover is coated with an anti-stick coating. Certainly, because the front end is designed to be blunt (non-puncturing), the irradiator cover made from zirconia porcelain can also satisfy the design requirements of the present invention.

The shape of the front end of the irradiator 1 can be an arc surface, a flat surface, a combination of an arc surface and a flat surface, a combination of an arc surface and an arc surface, or a combination of a flat surface and a flat surface. As shown in FIG. 1, in this embodiment, the irradiator 1 has a cylindrical structure. The length of the irradiator is 180 mm, and the diameter is 1.3 mm.

This embodiment further provides a specific structure of the front end of the antenna. The antenna of the present invention includes a needle bar 3 disposed on a rear portion of the irradiator cover 2 and a coaxial cable disposed inside the needle bar 3 in a penetrating manner, and the coaxial cable includes an inner conductor 5 and an outer conductor 4. The irradiator 1 includes a hole opened backward, and the inner conductor 5 of the coaxial cable is inserted into the hole to be fixed to the irradiator 1. In this embodiment, the inner conductor 5 is fixed to the irradiator 1 in a welding manner, and in addition, a mechanical press fitting manner may alternatively be adopted, to ensure a conductive connection between the inner conductor 5 and the irradiator 1. The irradiator 1 is fixedly connected to the outer conductor 4 of the coaxial cable (the irradiator is conductively connected to the outer conductor of the coaxial cable). The internal structure and the parameter of the antenna of this embodiment enable the center of microwave irradiation to be closer to the front end of the antenna, which is conducive to ablation treatment of GGO.

Because the center of microwave irradiation is closer to the front end of the antenna, and the antenna is relatively thin, a conventional water cooling structure cannot be applied to the antenna of this embodiment. Therefore, the inventor designs a novel water cooling structure for a microwave ablation antenna.

Specifically, a medium pipe 6 is disposed inside the needle bar, and is sleeved outside the irradiator 1 and the coaxial cable. The wall thickness of the medium pipe 6 ranges from 0.02 to 0.04 mm. The medium pipe 6 is made from polyetheretherketone. A hole is provided as a water inlet/outlet of cooling water in a front end of the medium pipe 6 or/and a sidewall of the front end; a first gap 7 is formed between the medium pipe 6 and the irradiator cover 2 and between the medium pipe 6 and the needle bar 3, and the first gap 7 serves as a water inlet passage of the cooling water; and a second gap 8 is formed between the medium pipe 6 and the irradiator 1 and between the medium pipe 6 and the outer conductor 5 of the coaxial cable, and the second gap 8 serves as a water return passage of the cooling water. The rear end of the needle bar 3 is provided with a water inlet chamber and a water outlet chamber. The water inlet chamber is connected to the water inlet passage, the water outlet chamber is connected to the water return passage, the water inlet chamber is connected to a water source of the cooling water through a pipeline, the water outlet chamber is connected to a water drawing apparatus through the pipeline, the water drawing apparatus works to draw cooling water from the water inlet chamber into the water inlet passage, and subsequently, the cooling water enters the water return passage through the water inlet/outlet of the medium pipe, then, enters the water outlet chamber, and is drawn out, so that water cooling is implemented. Deionized water or physiological saline may also be selected as a cooling medium.

Certainly, using the second gap 8 as a water inlet passage of the cooling water and the first gap 7 as a water return passage of the cooling water is also a feasible alternative solution. In this embodiment, a water drawing apparatus is selected to provide a driving force for flowing of the cooling water because in consideration of small cross-sectional areas of the water inlet passage and the water return passage, if a water pump is used to drive a water flow, a problem of relatively high resistance is brought, using a water drawing apparatus leads to easier implementation. Certainly, using the water pump for driving is also a feasible alternative solution.

Practice of the inventor shows that DNA of the GGO tissue does not change before and after ablation. Therefore, the inventor assumes that if the step of biopsy of the GGO can be adjusted to be performed after ablation, damage to the GGO tissue cells during a conventional biopsy process can be avoided, thereby eliminating a risk of cancer metastasis.

To more accurately perform biopsy sampling on the GGO tissue after ablation, in the antenna of this embodiment, a groove 9 is provided in a sidewall of the irradiator cover 2, and the groove 9 is provided close to the irradiator 1. Because of the characteristics of the lung tissue, after the irradiator cover 2 provided with the groove 9 is inserted into the lungs, the groove 9 is immediately filled up with the lung tissue. Microwave ablation causes the lung tissue at the groove to be burned and solidified. After the antenna is pulled out, the lung tissue at the groove appears to protrude outward, and can be easily identified in the image. Biopsy sampling can be performed on the tissue protruding outward, to obtain a tissue sample near the center of microwave irradiation.

Figure 2:
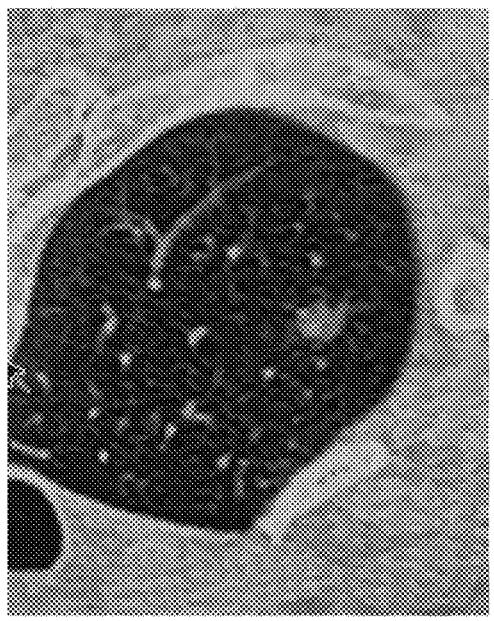
FIG. 2 is an image of the lungs before ablation.
Figure 3:
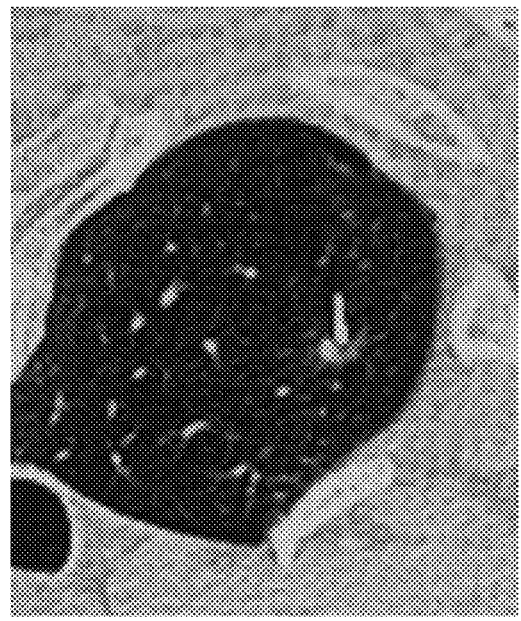
FIG. 3 is an image of the lungs during ablation.

The inventor carried out GGO ablation experiments (non-public) by using the microwave ablation antenna according to Embodiment 1. FIG. 2 and FIG. 3 are images of the lungs before and during ablation. The white areas on the right in the center of FIG. 2 and FIG. 3 are GGO. It can be seen from FIG. 3 that the microwave ablation antenna pushes the GGO and deforms it (but does not puncture the lesion), thereby making the lesion denser while obvious reducing the volume of the lesion, and reducing a range of ablation. Therefore, the entire lesion can be coagulated by using lower microwave irradiation energy, to protect the lung tissue to the greatest extent. Microwaves of conventional microwave ablation antennas are all irradiated backward. The special structure of the antenna of this embodiment makes the irradiation center located at the front end of the antenna, forward irradiation energy dominant, and irradiation energy of the antenna exactly match the GGO that is pushed to deform. Therefore, the antenna of the present invention is better adapted to the non-destructive ablation of GGO (an ablation method without penetrating through the interior and the outside of the lesion), and can completely ablate the tumor without creating a passage inside and outside the tumor or causing release of liquids, such as body fluids, inside the tumor because of internal high pressure after heating.

Embodiment 2

Figure 4:
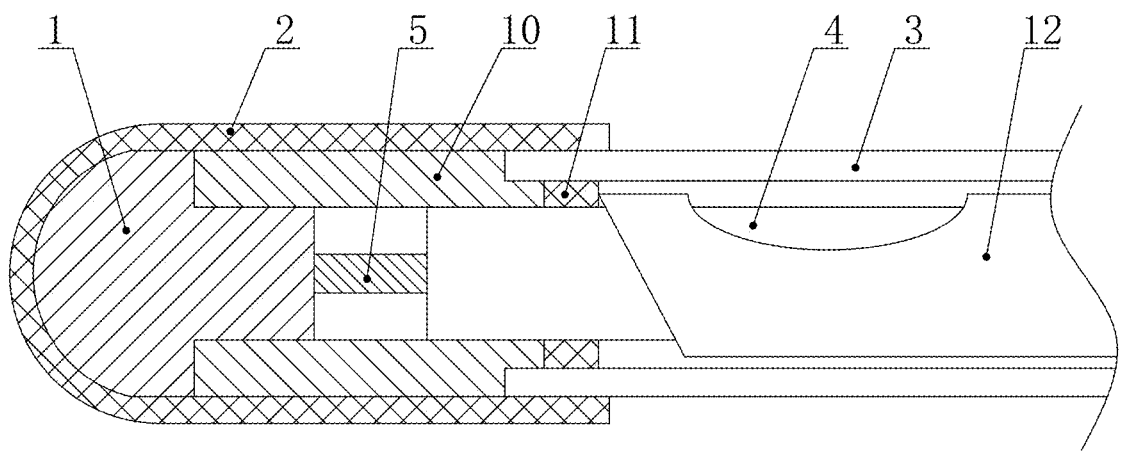
FIG. 4 is a partial cross-sectional view of a front end of a microwave ablation antenna according to Embodiment 2.

As shown in FIG. 4, the antenna includes an irradiator 1 (a front end of a head is an arc surface) made of metal, a medium sleeve 10 sleeved behind the irradiator 1, and a needle bar 3 sleeved on a rear end of the medium sleeve 10, where a coaxial cable is disposed inside the needle bar 3 in a penetrating manner, the rear end of the irradiator 1 is connected (conductively connected) to an inner conductor 5 of the coaxial cable, and an emitting window of the antenna is formed between the rear end of the irradiator 1 and an outer conductor 4 of the coaxial cable. A water guide pipe 12 is disposed between the coaxial cable and the needle bar 3, and a front end thereof is fixed to a water plugging shaft 11. A gap between the water guide pipe 12 and the coaxial cable forms a water inlet passage, and a gap between the water guide pipe and the needle bar forms a water return passage.

The foregoing embodiment exemplifies two shapes of the front end of the irradiator (a flat head and a round head). In addition, other forms can also be adopted, for example, a combination of an arc surface and an arc surface, a combination of a flat surface and a flat surface, and a combination of an arc surface and a flat surface. The shape of the front end of the irradiation head is relatively smooth, so that the shape of the irradiation head without a puncturing function can achieve the objective of the present invention, and examples are not provided one by one in this embodiment of the present invention. The front end of the irradiator cover may also be round or flat. When the irradiator cover is made from an elastic material, a front end thereof is roughly the same as the front end of the irradiator, and when the irradiator cover is made from a non-elastic material, and the front end may be flat or round.

In addition, the present invention further claims application of the non-puncturing microwave ablation antenna in microwave ablation treatment of GGO.

In addition to the foregoing embodiments, the present invention may further include other implementations. Any technical solution formed by equivalent replacement or equivalent transformation falls within the protection scope claimed in the present invention.

What is claimed is:

1. A non-puncturing microwave ablation antenna, comprising;
   an irradiator located at a front end of the non-puncturing microwave ablation antenna;
   an irradiator cover sleeved on the irradiator, wherein a front end of the irradiator cover is blunt;
   a needle bar, disposed on a rear end of the irradiator cover; and
   a coaxial cable, disposed inside the needle bar in a puncturing manner;
   wherein
   the coaxial cable comprises an inner conductor and an outer conductor;
   the inner conductor is fixed to the irradiator, a medium pipe is sleeved over the irradiator and the coaxial cable, and a first hole is provided as a water inlet/outlet of cooling water in a front end of the medium pipe or/and a sidewall of the front end of the medium pipe;
   a first gap is formed between an outer surface of the medium pipe and the irradiator cover and between the outer surface of the medium pipe and the needle bar;

a second gap is formed between an inner surface of the medium pipe and the irradiator and between the inner surface of the medium pipe and the outer conductor of the coaxial cable; and the first gap serves as a water inlet passage of the cooling water, and the second gap serves as a water return passage of the cooling water; or the second gap serves as the water inlet passage of the cooling water, and the first gap serves as the water return passage of the cooling water.

2. The non-puncturing microwave ablation antenna according to claim 1, wherein the irradiator cover is entirely made from an elastic material or the front end of the irradiator cover is made from the elastic material.

3. The non-puncturing microwave ablation antenna according to claim 1, wherein a length of the irradiator ranges from 160 to 200 mm, a diameter of the irradiator ranges from 1.1 to 1.5 mm, and a thickness of the irradiator cover ranges from 0.2 mm to 0.5 mm.

4. The non-puncturing microwave ablation antenna according to claim 1, wherein a groove is provided in a sidewall of the irradiator cover.

5. The non-puncturing microwave ablation antenna according to claim 1, wherein the irradiator comprises a second hole, wherein the second hole is opened backwards, and the inner conductor of the coaxial cable is inserted into the second hole and is fixed to the irradiator.

6. The non-puncturing microwave ablation antenna according to claim 1, wherein the inner conductor of the coaxial cable is fixed to the irradiator in a welding manner or in a press fitting manner.

7. The non-puncturing microwave ablation antenna according to claim 1, wherein the irradiator is fixedly connected to the outer conductor of the coaxial cable, and the irradiator is conductively connected to the outer conductor of the coaxial cable.

8. The non-puncturing microwave ablation antenna according to claim 5, wherein the medium pipe is made from polyetheretherketone, and a wall thickness of the medium pipe ranges from 0.02 to 0.04 mm.

9. The non-puncturing microwave ablation antenna according to claim 1, wherein the non-puncturing microwave ablation antenna is applied to a microwave ablation treatment of lung ground glass opacity.

10. The non-puncturing microwave ablation antenna according to claim 2, wherein the non-puncturing microwave ablation antenna is applied to a microwave ablation treatment of lung ground glass opacity.

11. The non-puncturing microwave ablation antenna according to claim 3, wherein the non-puncturing microwave ablation antenna is applied to a microwave ablation treatment of lung ground glass opacity.

12. The non-puncturing microwave ablation antenna according to claim 4, wherein the non-puncturing microwave ablation antenna is applied to a microwave ablation treatment of lung ground glass opacity.

13. The non-puncturing microwave ablation antenna according to claim 5, wherein the non-puncturing microwave ablation antenna is applied to a microwave ablation treatment of lung ground glass opacity.

14. The non-puncturing microwave ablation antenna according to claim 6, wherein the non-puncturing microwave ablation antenna is applied to a microwave ablation treatment of lung ground glass opacity.

15. The non-puncturing microwave ablation antenna according to claim 7, wherein the non-puncturing microwave ablation antenna is applied to a microwave ablation treatment of lung ground glass opacity.

16. The non-puncturing microwave ablation antenna according to claim 8, wherein the non-puncturing microwave ablation antenna is applied to a microwave ablation treatment of lung ground glass opacity.

* * * * *